(12) United States Patent  (10) Patent No.: US 9,314,214 B2
Russak et al.  (45) Date of Patent: Apr. 19, 2016

(54) CALIBRATION OF RADIOGRAPHIC IMAGES

(75) Inventors: Zeev Russak, RaAnana (IL); Zeev Glozman, Tel-Aviv (IL)

(73) Assignee: Brainlab Ltd., Petach-Tikva (IL)

( * ) Notice: Subject to any disclaimer, the term of this patent is extended or adjusted under 35 U.S.C. 154(b) by 1310 days.

(21) Appl. No.: 11/519,909

(22) Filed: Sep. 13, 2006

(65) Prior Publication Data

US 2008/0063304 A1  Mar. 13, 2008

(51) Int. Cl.
G06K 9/32  (2006.01)
A61B 6/12  (2006.01)
A61B 6/00  (2006.01)

(52) U.S. Cl.
CPC .. *A61B 6/12* (2013.01); *A61B 6/583* (2013.01)

(58) Field of Classification Search
USPC ........... 600/426, 414; 356/396; 382/298, 281, 382/283, 199
See application file for complete search history.

(56) References Cited

U.S. PATENT DOCUMENTS

| | | |
|---|---|---|
| 3,069,654 A | 12/1962 | Hough |
| 3,812,842 A | 5/1974 | Rodriguez |
| 4,506,676 A | 3/1985 | Duska |
| 4,870,694 A | 9/1989 | Takeo |
| 5,394,457 A | 2/1995 | Leibinger et al. |
| 5,469,847 A | 11/1995 | Zinreich et al. |
| 5,506,918 A | 4/1996 | Ishitani |
| 6,246,783 B1 * | 6/2001 | Avinash .......... 382/128 |
| 7,079,620 B2 | 7/2006 | Vaillant et al. |
| 7,127,090 B2 | 10/2006 | Kreang-Arekul et al. |
| 7,480,363 B2 | 1/2009 | Lasiuk et al. |
| 7,616,818 B2 | 11/2009 | Dewaele |
| 2002/0009229 A1 * | 1/2002 | Fu et al. .......... 382/199 |
| 2004/0086082 A1 * | 5/2004 | Foos et al. .......... 378/163 |
| 2007/0260137 A1 | 11/2007 | Sato et al. |
| 2008/0063302 A1 | 3/2008 | Russak et al. |
| 2008/0063304 A1 | 3/2008 | Russak et al. |

OTHER PUBLICATIONS

Margrit Betke et al, Real-time multiple vehicle detection and tracking from a moving vehicle, Machive Vision and Applications 2000.*
T.J. Atherton et al, Size invariant circle detection, Image and Vision Computing 1999.*
Thomas Lehmann et al, Survey:Interpolation Methods in Medical Image Processing, IEEE 1999.*
Carolyn Kimme et al, Finding Circles by an Array of Accumulators, ACM 1975.*
M. Atiquzzaman, Multiresolution Hough Transform—An efficient Method of Detecting Patterns in Images, IEEE 1992.*
Michele Ceccarelli et al, Circle Detection Based on Orientation Matching, IEEE 2001.*
Chen (Li-Qun Chen, A visual attention model for adapting images on small displays, IEEE 2003).*

(Continued)

*Primary Examiner* — Mark Roz

(57) ABSTRACT

Apparatus for calibrating an image, the image comprising a spherical marker, the apparatus comprising: an image receiver, configured to receive the image, and a marker finder, associated with the image receiver and configured to automatically find an image of the marker in the received image.

27 Claims, 19 Drawing Sheets

(56) References Cited

OTHER PUBLICATIONS

Official Action Dated Nov. 20, 2009 From the US Patent and Trademark Office Re.: U.S. Appl. No. 11/519,910.

Atherton et al. "Size Invariant Circle Detection", Image and Vision Computing, 17: 795-803, 1999.

Betke et al. "Real-Time Multiple Vehicle Detection and Tracking From a Moving Vehicle", Machine Vision and Applications, 12: 69-83, 2000.

Lehmann et al. "Survey: Interpolation Methods in Medical Image Processing", IEEE Transactions on Medical Imaging, 18(11): 1049-1075, Nov. 1999.

Response Dated Mar. 22, 2010 to Official Action of Nov. 20, 2009 From the US Patent and Trademark Office Re.: U.S. Appl. No. 11/519,910.

Notice of Allowance Dated Jun. 11, 2010 From the US Patent and Trademark Office Re. : U.S. Appl. No. 11/519,910.

\* cited by examiner

Figure 17

```
public class CCircle : IComparable, IHashCodeProvider, IComparer
{
    public PointF P;
    public float R;
    public int CompareTo(object obj)
    {
        if (Math.Abs(R-((CCircle)obj).R)<1)
            if(Math.Abs(P.X-((CCircle)obj).P.X)<1)
                if(Math.Abs(P.Y-((CCircle)obj).P.Y)<1) return
0;
        return (int)(R-((CCircle)obj).R);
    }
    #region IHashCodeProvider Members
    public int GetHashCode(object obj)
    {
        return P.GetHashCode()+R.GetHashCode();
    }
    #endregion
    #region IComparer Members
    public int Compare(object x, object y)
    {
        if(Math.Abs(((CCircle)x).R-((CCircle)y).R)<1)
            if(Math.Abs(((CCircle)x).P.X-((CCircle)y).P.X)<1)
                if(Math.Abs(((CCircle)x).P.Y-((CCircle)y).P.Y)<1) return
0;
        return (int)(((CCircle)x).R-((CCircle)y).R);
    }
    #endregion
}
```

CALIBRATION OF RADIOGRAPHIC IMAGES

FIELD AND BACKGROUND OF THE INVENTION

The present invention relates to calibration of images and more particularly, but not exclusively to an apparatus and method for calibration of radiographic images.

In the interpretation of images such as radiographic images, various approaches are known for differentiating between structures which appear in such images.

A major difficulty encountered when interpreting radiographic images is that the body is three dimensional. However, even if the patient is positioned is a known distance from the radiographic camera, the image plane may vary according to an organ or bone of interest. That is to say, the camera may zoom-in or zoom-out, so as to focus at the organ or bone of interest. Consequently, there arises a need to know the scale of the resultant radiographic image, in order to identify the organ (or bone) of interest, accurately estimate the bone dimensions, etc.

U.S. Pat. No. 4,506,676, to Duska, entitled "Radiographic localization technique", filed on Sep. 10, 1982, describes an adhesive, flexible tape which includes radiopaque dots. The tape is applied to a patient to identify an area of interest, and the image of the dot appears in the x-ray photograph as a pointer to the area.

U.S. Pat. No. 3,812,842, to Rodriguez, entitled "Method for locating blood vessels for catheterization", filed on Jan. 18, 1973, describes an indexing scale which includes markers that are visible in x-ray photographs. The markers facilitate locating a particular blood vessel relative to the scale in the x-ray photograph, and the arms which support the indexing device are secured to a patient's chest with adhesive tape.

U.S. Pat. No. 5,394,457, to Leibinger, entitled "Device for marking body sites for medical examinations", filed on Oct. 7, 1993, describes a device for marking body sites for imaging medical examinations. By using multiple markers, two x-ray exposures taken from different directions can be used to determine the spatial location of any desired point. The marker has a head with a cavity for receiving a substance which exhibits high contrast, and in one embodiment, a fixture which supports the marker is attached to the skin with an adhesive.

U.S. Pat. No. 5,469,847, to Zinreich, entitled "Radiographic multi-modality skin markers", filed on Feb. 28, 1994, describes an adhesive surface marker with a cavity for receiving imaging materials. The surface marker contains an x-ray opaque gel, such as barium sulfate, which is sealed on all sides by an outer casing. The use of multiple markers provides reference points which allow the geometrical calculation of the precise location of a particular site within a patient's body.

U.S. Pat. No. 7,079,620, to Vaillant, entitled "Method and apparatus for determining a magnification factor a radiographic image", filed on Mar. 13, 2002, describes a method and apparatus for determining a magnification factor in a radiography device of the type comprising an X-ray source and means for acquiring images placed facing the source.

With Vaillant, the source and the means for acquiring images is mounted so as to rotate about one axis with respect to a support on which an object to be X-rayed is intended to be positioned.

The method and the apparatus implementing the method comprises: acquiring two images corresponding to two different angular positions of the source and of the recording means with respect to the support; identifying on these images projections of one or more points of the X-rayed object; and determining the magnification factor of at least one of the images, first, as a function of the angular displacement of the source and of the recording means between the acquisitions of the images in question and, secondly, as a function of the positions on these images of the identified projections.

However, such solutions are not accurate enough, too cumbersome, or are inconvenient.

There is thus a widely recognized need for, and it would be highly advantageous to have, a system devoid of the above limitations.

SUMMARY OF THE INVENTION

According to one aspect of the present invention there is provided an apparatus for calibrating an image, the image comprising a spherical marker, the apparatus comprising: a) an image receiver, configured to receive the image, and b) a marker finder, associated with the image receiver and configured to automatically find an image of the marker in the received image.

Preferably, the apparatus of claim further comprises a calibrator, configured to calibrate the image, utilizing the found image of the marker.

Optionally, the apparatus of claim further comprises a digitizer, associated with the image receiver and configured to digitize the image, thereby generating the data.

According to a second aspect of the present invention there is provided a method for calibrating an image, the image comprising a spherical marker, the method comprising: a) receiving the image, and b) automatically finding an image of the spherical calibration marker in the received image.

Preferably, the method further comprises calibrating the image, utilizing the found image of the marker.

Optionally, the method further comprises a preceding step of digitizing the image for generating the data.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings.

With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Drawings:

FIG. 1a is a block diagram illustrating a radiographic imaging scenario, according to a preferred embodiment of the present invention.

FIG. 1b is a simplified block diagram illustrating an apparatus for calibrating an image according to a preferred embodiment of the present invention.

FIG. 1c is a detailed simplified block diagram illustrating an apparatus for calibrating an image according to a preferred embodiment of the present invention.

FIG. 2 is a simplified flowchart illustrating a method for calibrating an image according to a preferred embodiment of the present invention.

FIG. 3 shows an exemplary downsized image according to a preferred embodiment of the present invention.

FIG. 4 shows an exemplary edge detected image, generated using the Sobel Edge Detection Method, according to a preferred embodiment of the present invention.

FIG. 5 shows an exemplary binary image, according to a preferred embodiment of the present invention.

FIG. 6 illustrates an exemplary ring matrix, according to a preferred embodiment of the present invention.

FIG. 7 shows an exemplary convolved image, according to a preferred embodiment of the present invention.

FIG. 8 shows an exemplary resized convolved image, according to a preferred embodiment of the present invention.

FIG. 9 shows an exemplary image with a spherical calibration object found on the image, according to a preferred embodiment of the present invention.

Figure 10:
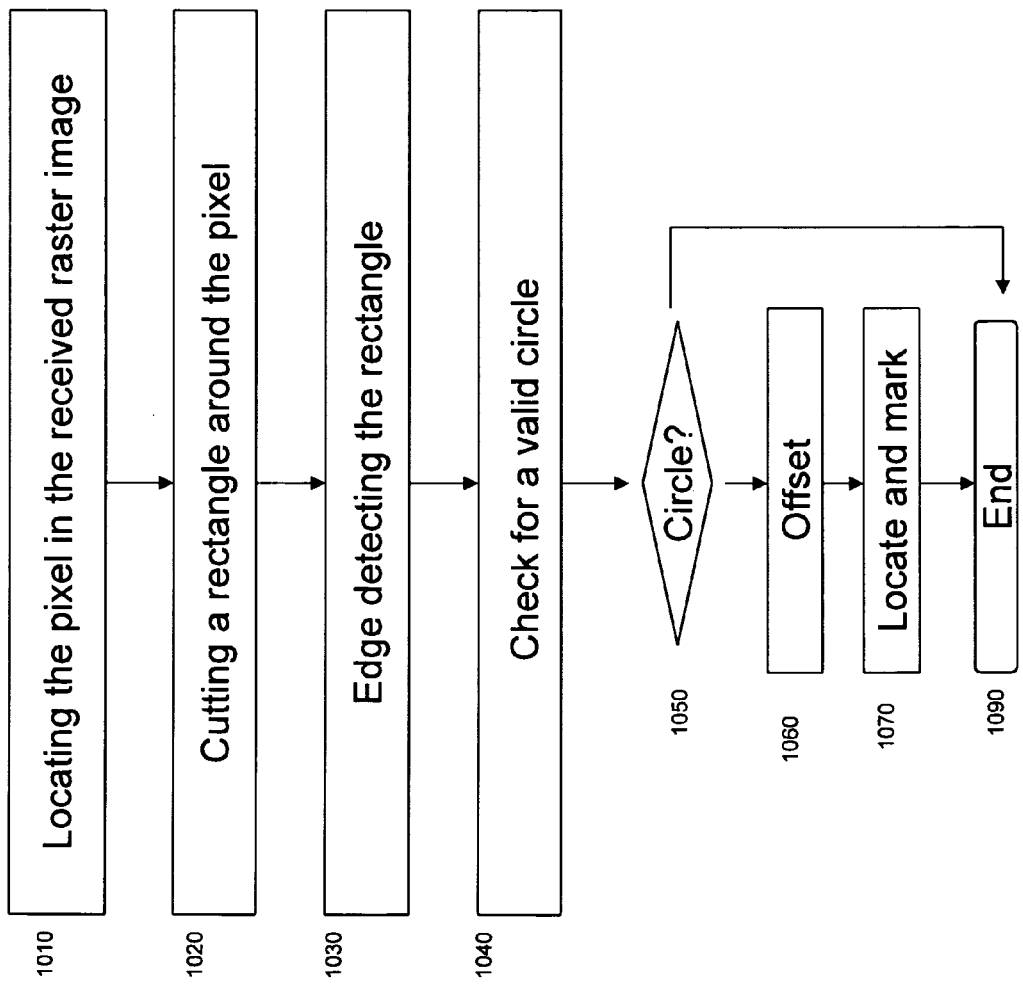

FIG. 10 is an exemplary flowchart of a method for checking if a pixel is inside a circle, according to a preferred embodiment of the present invention.

Figure 11:
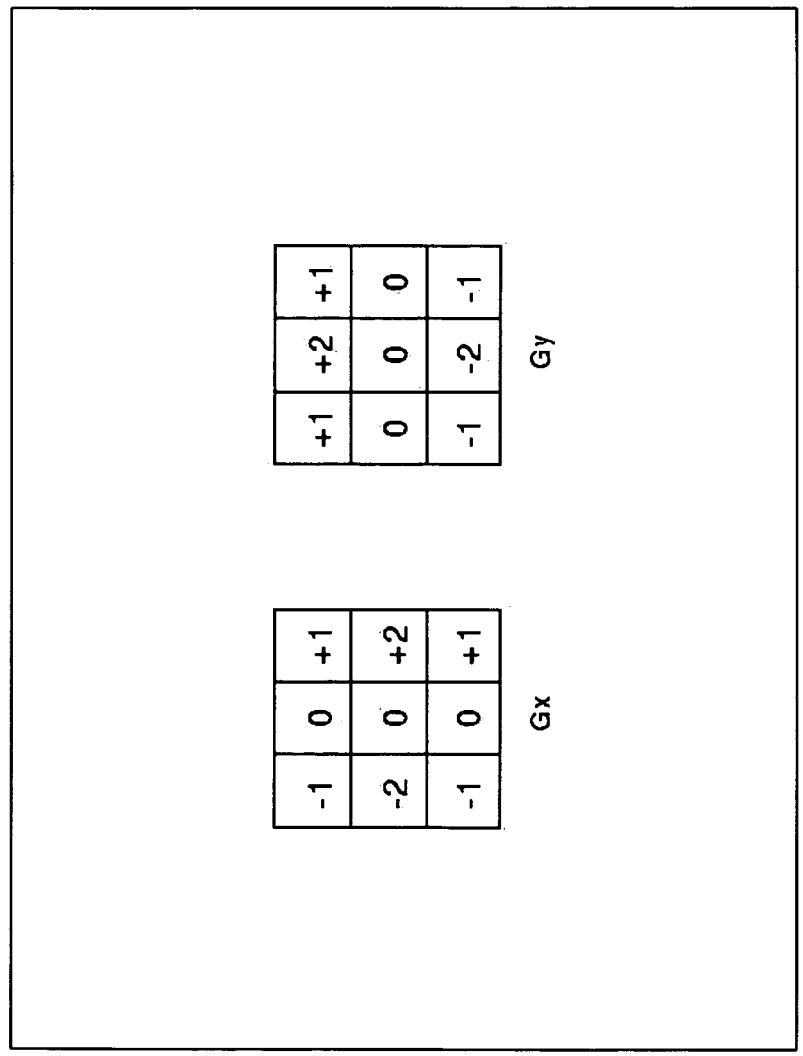

FIG. 11 shows exemplary convolution matrixes, according to a preferred embodiment of the present invention.

Figure 12:
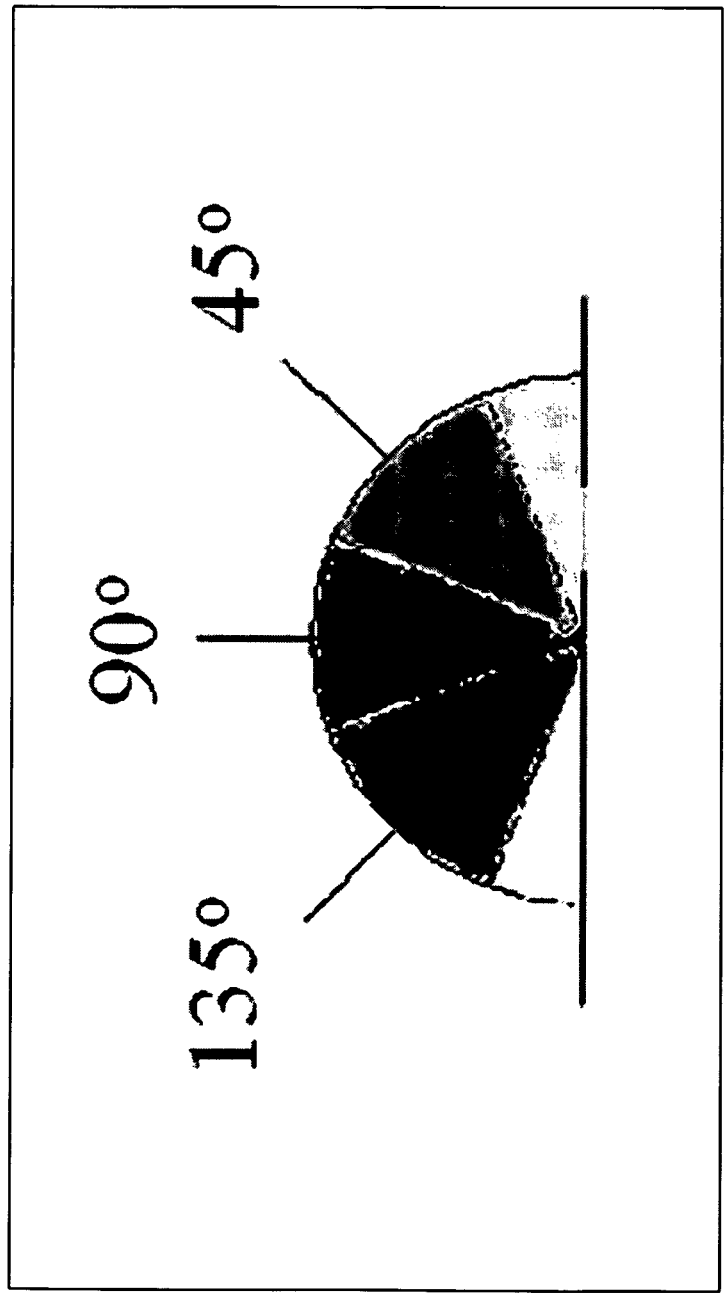

FIG. 12 illustrates edge direction rounding, according to a preferred embodiment of the present invention.

Figure 13:
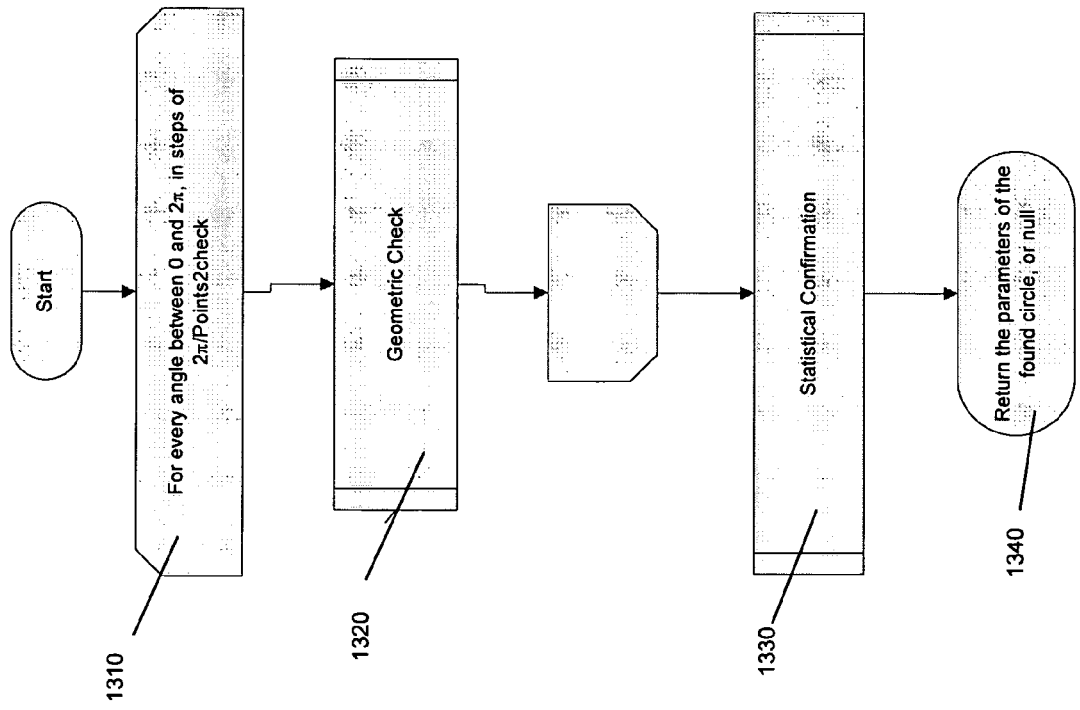

FIG. 13 is a flowchart illustrating a method for checking if edges surrounding a pixel form a circle, according to a preferred embodiment of the present invention.

Figure 14:
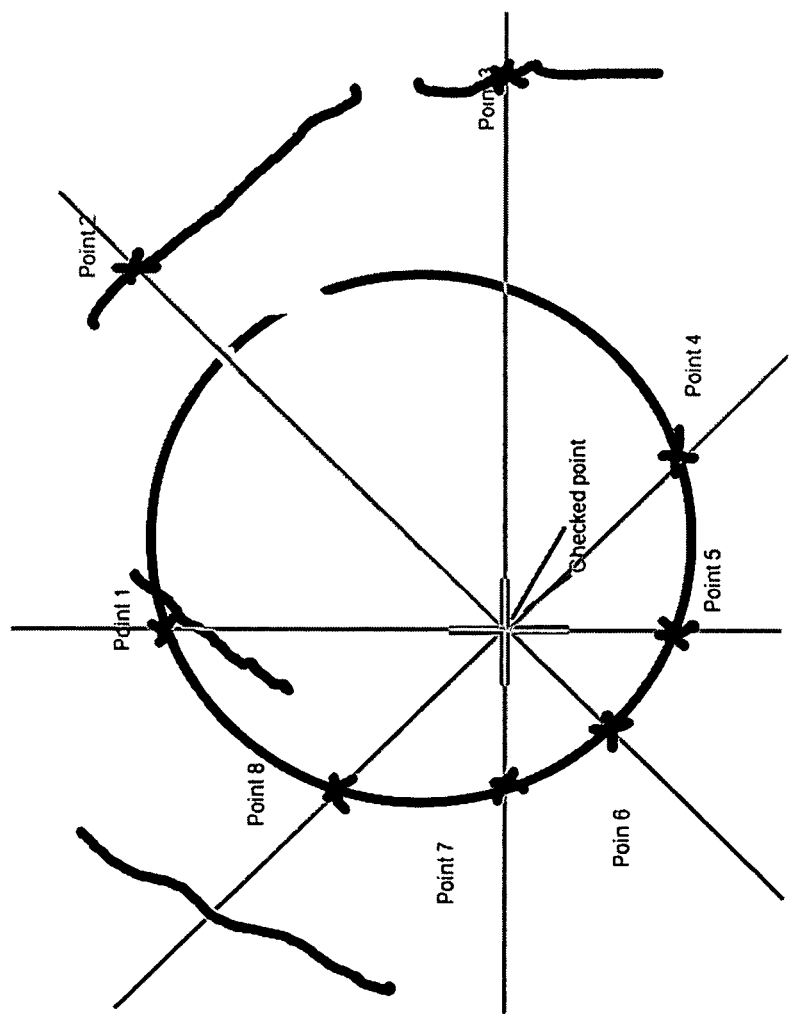

FIG. 14 illustrates an exemplary circularity check, according to a preferred embodiment of the present invention.

Figure 15:
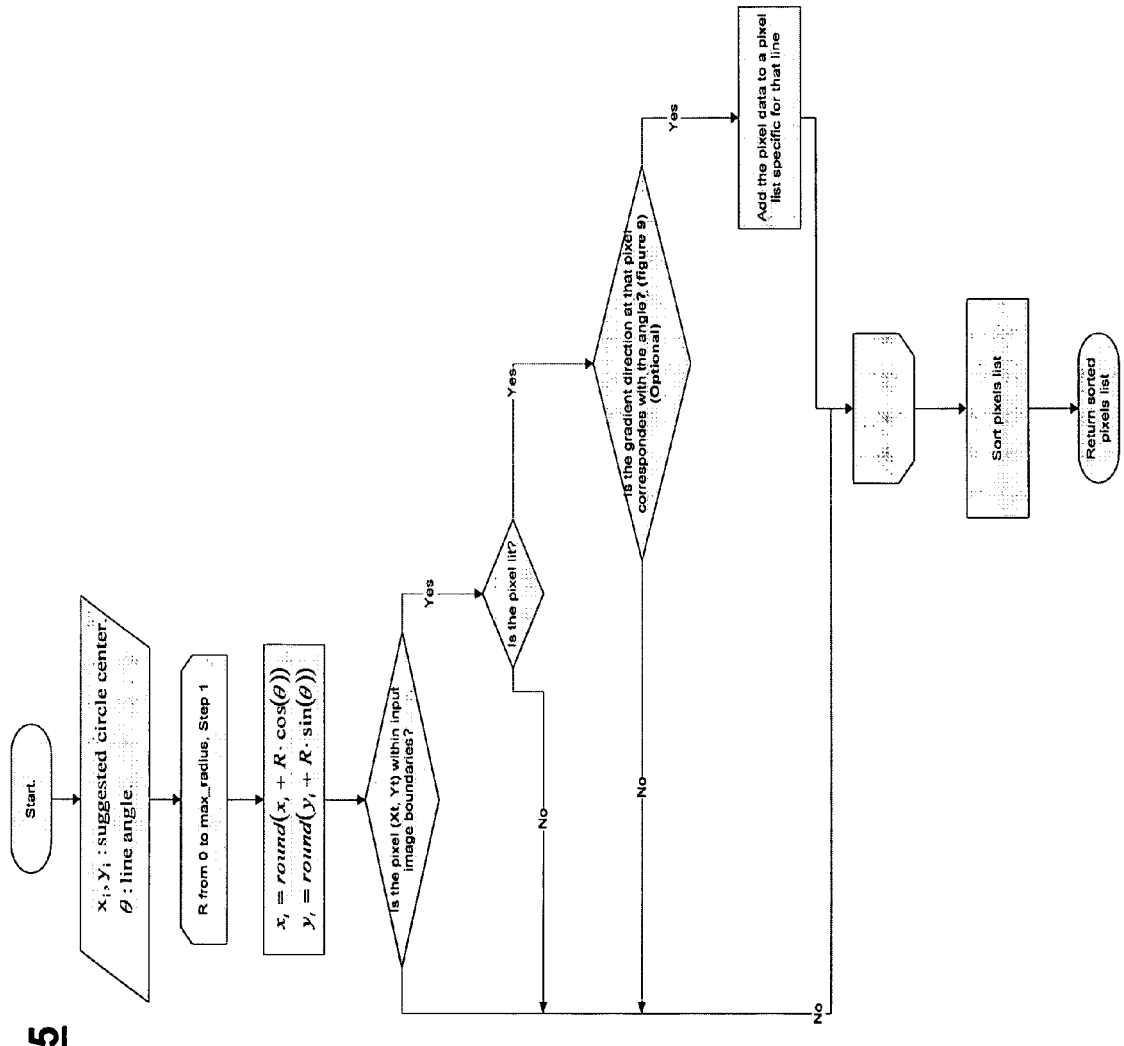

FIG. 15 is a flowchart illustrating an exemplary method for geometrically checking circularity around a pixel, according to a preferred embodiment of the present invention.

Figure 16:
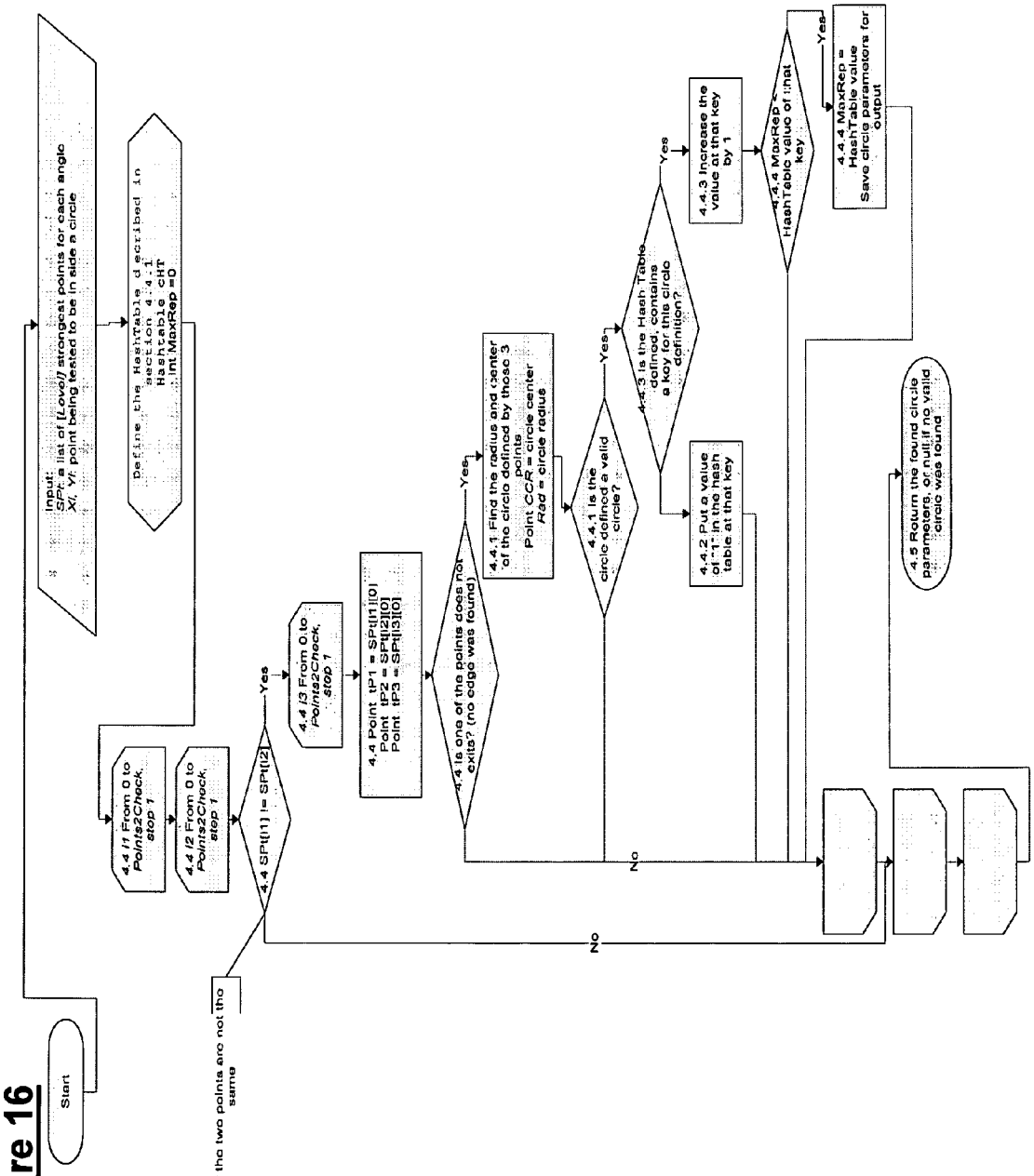

FIG. 16 is a flowchart illustrating a method for statistically confirming circularity, according to a preferred embodiment of the present invention.

FIG. 17 shows an exemplary Hash Class written in the C# Programming Language, according to a preferred embodiment of the present invention.

DESCRIPTION OF THE PREFERRED EMBODIMENTS

The present embodiments comprise an apparatus and a method for calibrating an image through finding a spherical calibration marker in the image.

Present embodiments of the present invention may be used for calibrating radiographic images.

While the body organs are three dimensional, a regular radiographic image is planar or two-dimensional. Even if the patient is at a fixed distance from a radiographic camera, the image plane may depend on the position of the bone or organ of interest.

Figure 1A:
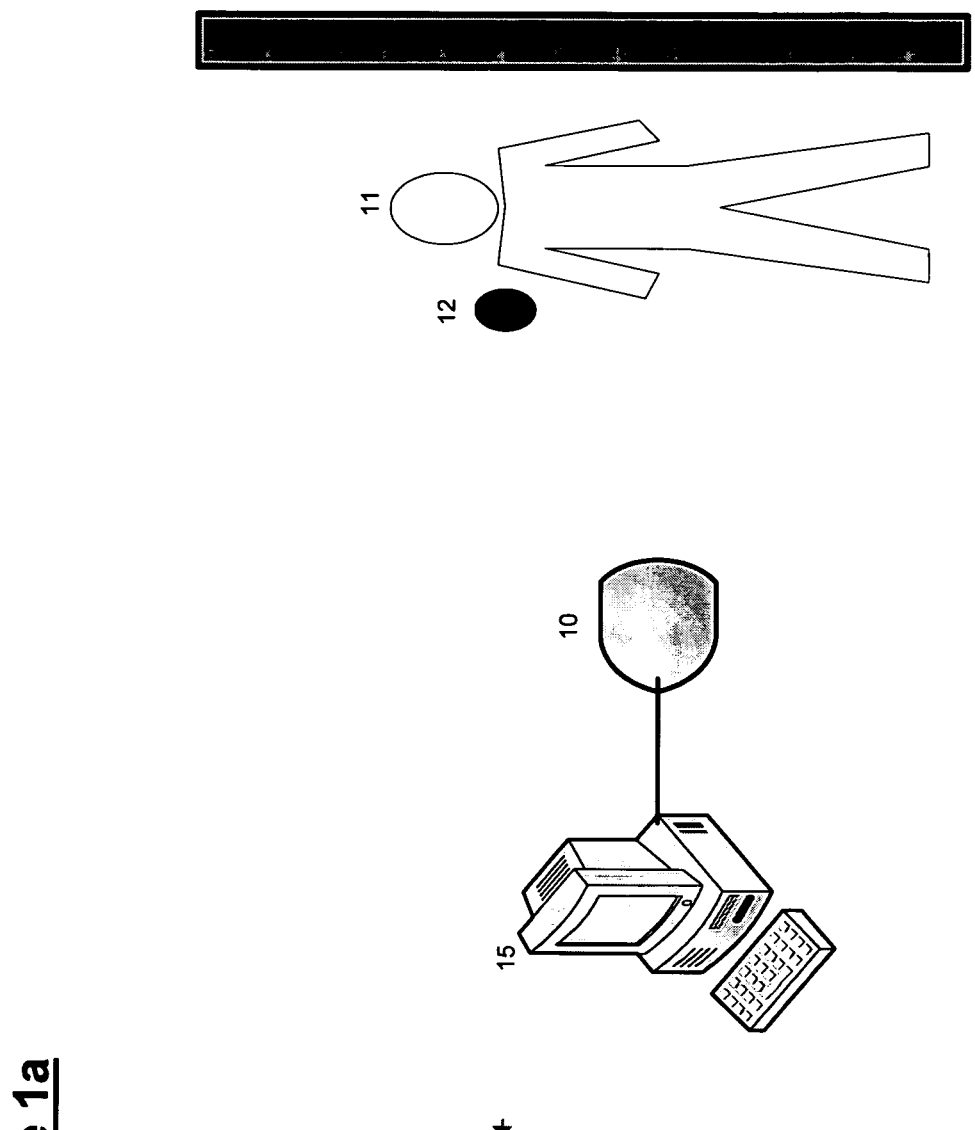

Reference is now made to FIG. 1a, which is a block diagram illustrating a radiographic imaging scenario, according to a preferred embodiment of the present invention.

As shown in FIG. 1a, a patient 11 may be imaged using an X-ray camera 10 together with a spherical calibration marker 12 positioned next to the patient 11. A spherical calibration marker 12 has the advantage of having the same circular image, regardless of the position of the camera 10 relative to the marker 12. However, the size of the circular image is typically proportional to $1/d^2$, where d is the distance between the camera 10 and the spherical calibration marker 12.

Typically, the X-ray camera 10 may zoom in, as in a regular camera so that different bones appear the same size in the final image. The spherical calibration marker 12 is positioned next to the patient, so that the maker 12 gives a concept of scale no matter what zoom is used Preferably, the image captured by the camera 10 is digitized and forwarded to a computer 15 implementing an apparatus for calibrating an image, as described in further detail hereinbelow.

Preferred embodiments of the present invention teach a method for finding an image of a spherical calibration method in an image, thereby calibrating the image.

The method may utilize a modified Hough transform to find possible circle centers in the image, and then verify each circle center using a geometric method and a statistic method, as described in further detail hereinbelow.

The principles and operation of a system and a method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Figure 1B:
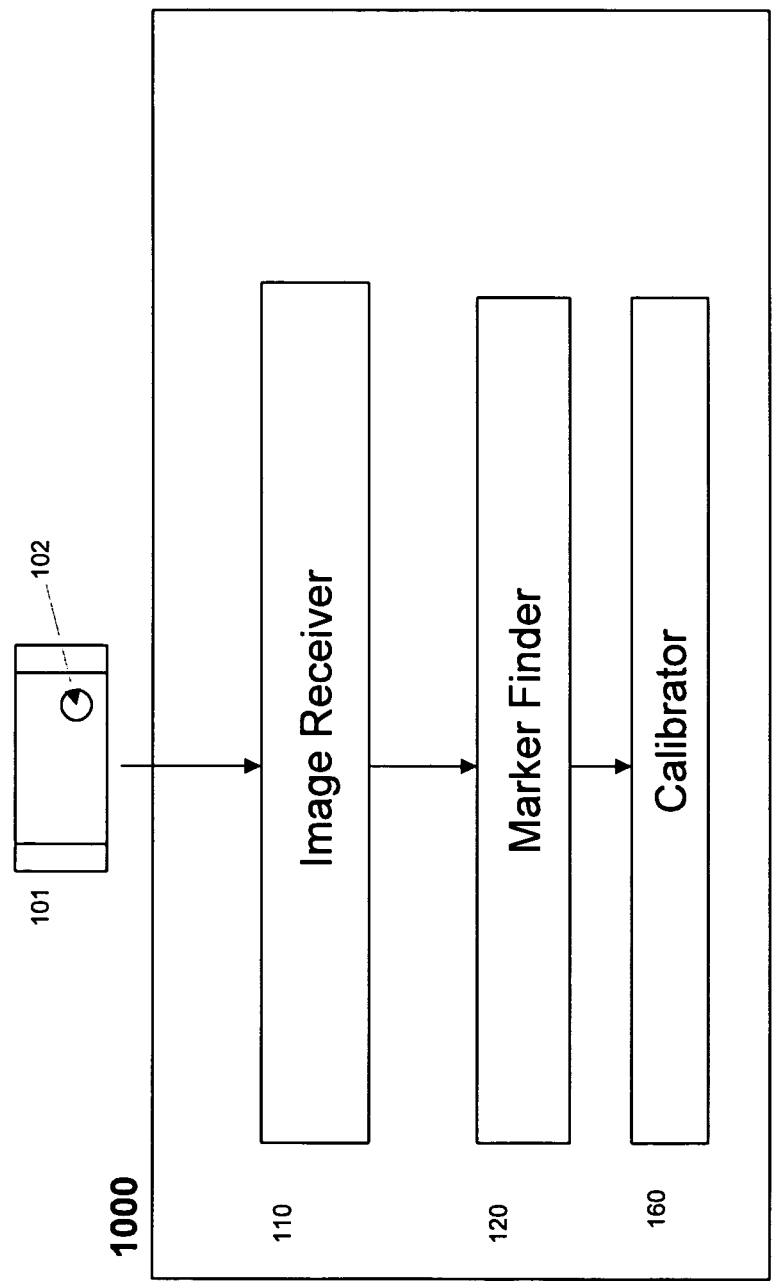

Reference is now made to FIG. 1b, which is a simplified block diagram illustrating an apparatus for calibrating an image according to a preferred embodiment of the present invention.

Apparatus 1000 includes an image receiver 110, for receiving the image 101.

The received image may be an image, say a large grey scale digital image, such as a radiographic image of a patient's organ, as known in the art. Preferably, the image 101 includes an image of a spherical calibration marker, as known in the art.

Preferably, the image receiver 110 is connected to a digitizer, such as a scanner, which digitizes the received image. The digitizer generates data representative of the image.

The apparatus 1000 further includes a marker finder 120, connected with the image receiver 110.

The marker finder 120 automatically finds an image of a spherical calibration marker 102 in the image 101, thereby providing a calibration for the image.

Preferably, apparatus 1000 also includes a calibrator 160. The calibrator 160 calibrates the image 102 using the imprint of a spherical calibration marker 102 found in the image 101. For example, the calibrator 160 may mark the image of the marker 102 on the image 101 with data pertaining to the diameter of the spherical object, etc, as described in further detail hereinbelow.

Figure 1C:
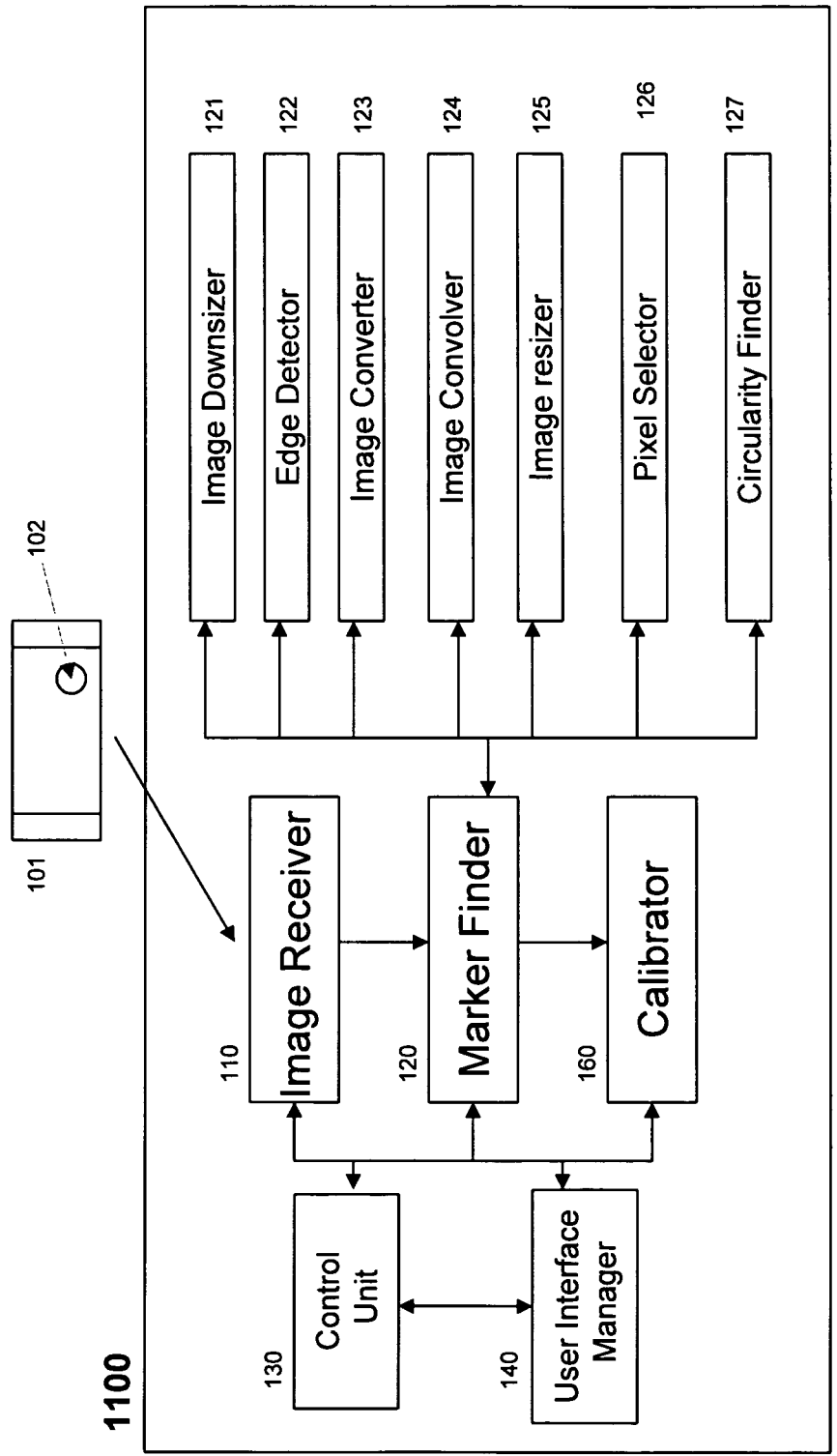

Reference is now made to FIG. 1c, which is a simplified block diagram illustrating an apparatus for calibrating an image according to a preferred embodiment of the present invention.

Apparatus 1100 includes an image receiver 110, a marker finder 120, and a calibrator 130, as described in further detail hereinabove.

Apparatus 1100 also includes an image downsizer 121 connected with the marker finder 120.

The image downsizer 121 downsizes the image into a downsized image having a smaller number of pixels than the image, as described in further detail hereinbelow.

Optionally, the apparatus 1100 also includes an edge detector 122, for detecting edges in the image downsized using the image downsizer 121, as described in further detail hereinbelow.

Optionally, apparatus 1100 also includes an image converter 123.

The image converter 123 converts the edge detected image into a binary image, by applying a predefined threshold on intensity of each pixel of the edge detected image. Preferably, the threshold is a quotient of intensity of a most intensive pixel of the edge detected image and an edge ratio predefined by a user, as described in further detail hereinbelow.

Optionally, apparatus 1100 also includes an image convolver 124.

The image convolver 124 convolves the binary image using a ring matrix, as described in further detail hereinbelow.

Optionally, apparatus 1100 also includes an image re-sizer 125, for further resizing the convolved binary image.

Preferably, the image resizer 125 generates a resized image where each pixel corresponds to half a minimal value defined by a user of the apparatus 1100, as described in further detail hereinbelow.

Optionally, apparatus 1100 also includes a pixel selector 126.

The pixel selector 126 sorts pixels of the resized image according to intensity of each of the pixels. The pixel selector 126 also selects a user defined number of strongest ones of the sorted pixels as potential marker pixels, as described in further detail hereinbelow.

Optionally, apparatus 1100 further includes a circularity finder 127.

The circularity finder 127 locates each of the selected pixels in the received image. The circularity finder 127 further finds out if each of the selected pixels is positioned in a circle surrounding the pixel in the image, as described in further detail hereinbelow.

Optionally, the marker finder 120 locates the spherical calibration marker on the selected pixels found to be positioned in a circle, as described in further detail hereinbelow.

Preferably, the apparatus 1100 further includes a control unit 130, communicating with the image receiver 110 and with marker finder 120.

The control unit 130 may be used for controlling the calibration process and for defining parameters for the methods implemented by the marker finder 120, as described in further detail hereinbelow.

Preferably, apparatus 1100 further includes a user interface manager 140, connected with the marker finder 120 and with the control unit 130. The user interface manager 140 manages an interface for interacting with a user of the apparatus 1100.

The interface may be used for presenting the image 102 with the spherical calibration marker 102 found on the image 101, for presenting other images to the user (say, the image 101 as received), for receiving parameters controlling methods implemented by the apparatus 1100, for finding the image of the spherical calibration marker 102 in the image 101, etc.

Methods employed by the apparatus 1100 for finding the image of the spherical calibration marker 102 in the received digital image 101 are described in further detail herein below.

Figure 2:
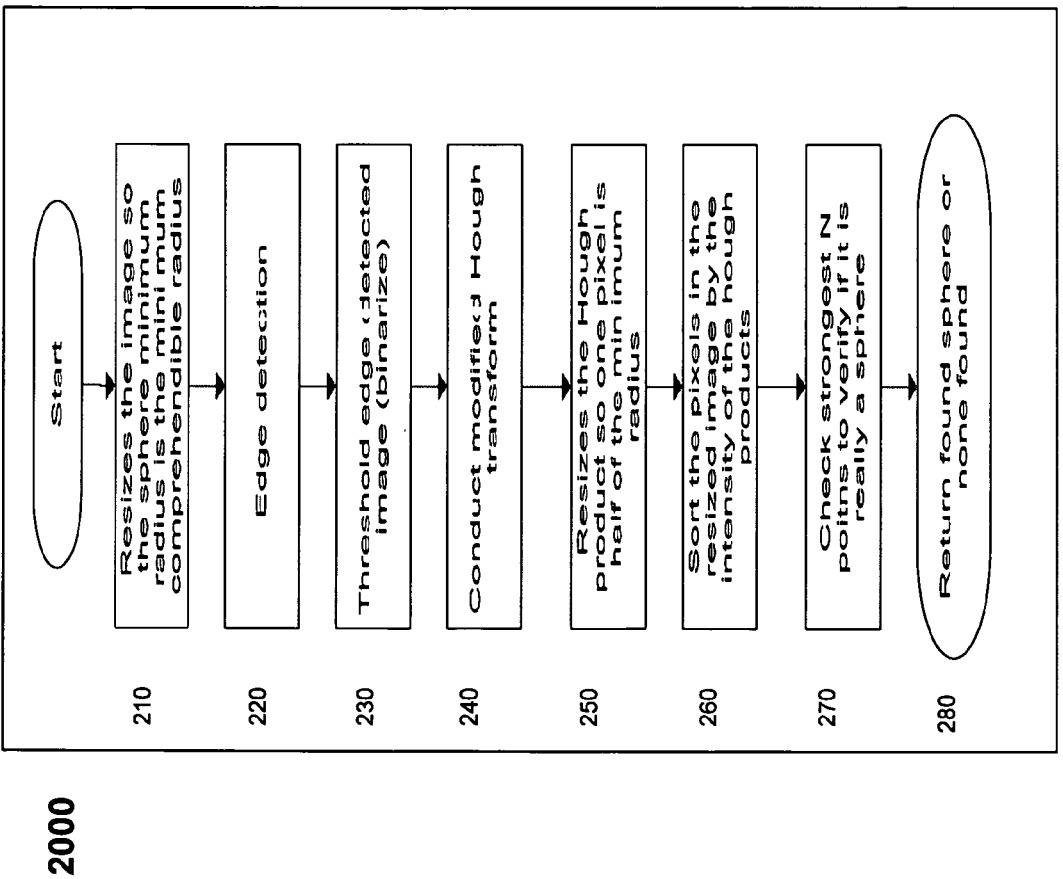

Reference is now made to FIG. 2, which is a simplified flowchart illustrating a method for calibrating an image according to a preferred embodiment of the present invention.

According to method 2000, an image which includes an image of a spherical calibration marker is received, say by the image receiver 110, as described in further detail hereinabove.

The received digital image is then processed, say by the marker finder 120 described hereinabove.

First, the image is downsized 210 into a downsized image having a smaller number of pixels than the image, say by the image downsizer described hereinabove.

The downsizing of the image allows faster calibration of the image, while keeping enough of the information of the received digital image for later processing.

For example, the faster calibration may allow surgeons to analyze radiographic images taken in real time, during a surgical procedure, in a much faster manner.

Preferably, the downsizing 210 of the image is carried such that a maximum expected radius of the spherical calibration marker is downsized into a predefined minimum comprehensible radius.

More preferably, a user of the apparatus 1000 is allowed to define the size of the minimum comprehensible radius, say using the control unit 130 described hereinabove. The user is further allowed to define the maximum radius expected for the image of the spherical calibration marker in the received digital image.

A Zoom Factor may than be calculated using the formula:

$$ZoomFactor = \frac{MinimumRadius}{MaximumRadius}$$

Preferably, the minimal comprehensible radius is selected by the user such that a circle having the minimal radius is the smallest circle detectable using the following steps of method 2000.

Preferably, if the maximum the maximum radius expected for the image of the spherical calibration marker is smaller than the smallest circle detectable using the following steps of method 2000, the image is not downsized.

Preferably, the minimal comprehensible radius is the radius of the smallest circle clearly which may be presented on a monitor screen. Typically, the smallest circle clearly shown on a monitor screen is a twenty pixels long radius.

Figure 3:
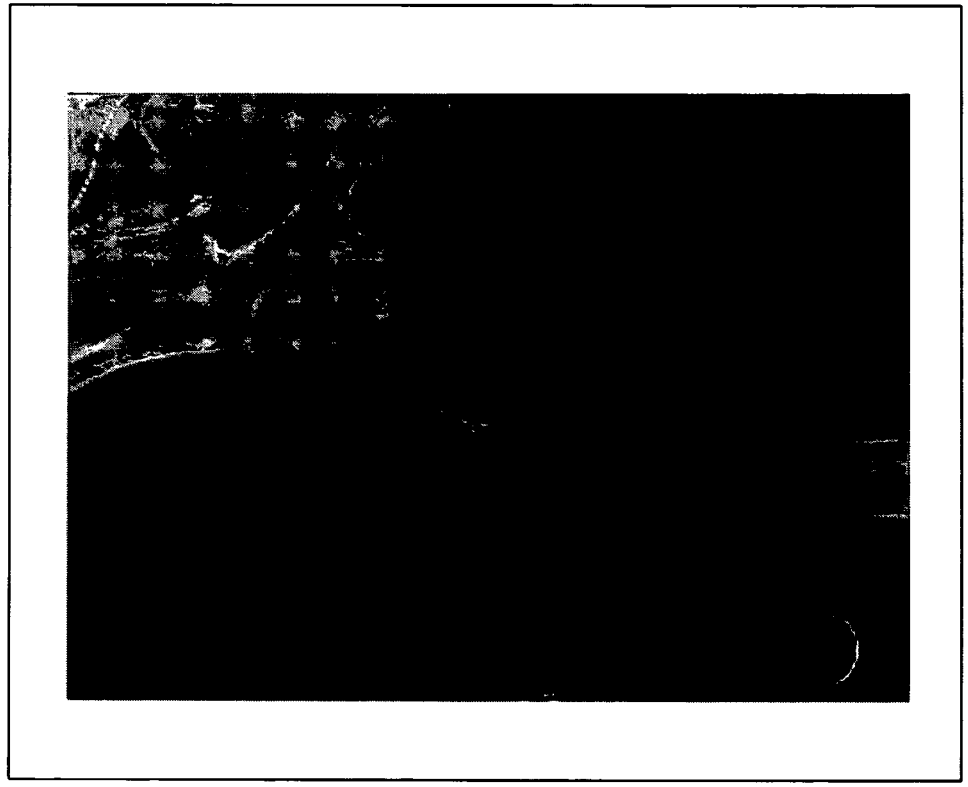

An exemplary downsized digital image according to a preferred embodiment of the present invention is shown in FIG. 3.

Next, the downsized digital image is edge detected 220, using the Sobel Edge Detection Method, or the Canny Edge Detection Method, or any other edge detection method, as known in the art. The edge detection may be carried out by the edge detector described hereinabove.

The goal of edge detection is to mark the points in the image at which luminous intensity changes sharply. The sharp changes in the intensity usually reflect important events and changes in properties of the image. The changes include but are not limited to: discontinuities in depth, discontinuities in surface orientation, changes in material properties, and variations in illumination.

Edge detection of an image reduces significantly the amount of data and filters out information that may be regarded as less relevant, preserving the important structural properties of an image.

There are many methods for edge detection, but most of the edge detection methods can be grouped into two categories: search-based methods, and zero-crossing based methods.

The search-based methods detect edges by looking for maxima and minima in the first derivative of the image, usually local directional maxima of the gradient magnitude.

The zero-crossing based methods search for zero crossings in the second derivative of the image in order to find edges, usually the zero-crossings of the Laplacian or the zero-crossings of a non-linear differential expression, as known in the art.

Figure 4:
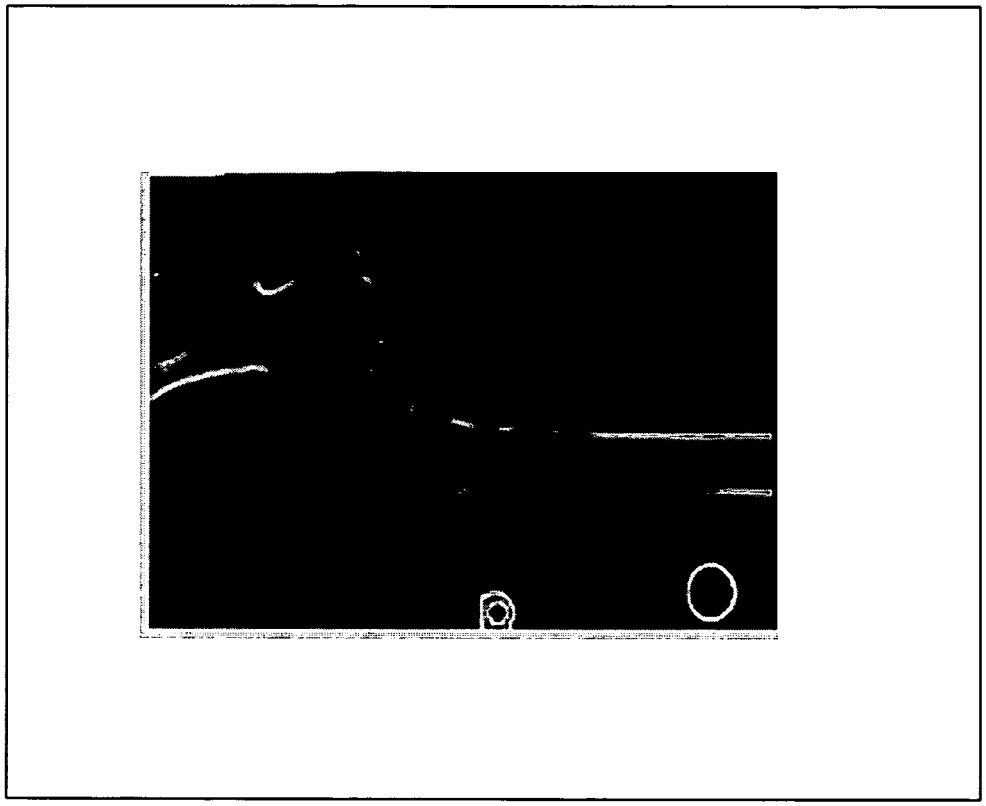

An exemplary edge detected image, generated using the Sobel Edge Detection Method, according to a preferred embodiment of the present invention is shown in FIG. 4.

Next, the edge detected image is converted 230 into a binary image, say using the image converter described hereinabove.

Preferably, the conversion into the binary image is carried out using a threshold. Preferably, the threshold is calculated by dividing the intensity of the most intensive pixel of the edge detected image by an Edge Ratio Parameter:

$$Threshold = \frac{MaxIntensivePixel}{EdgeRatioParameter}$$

The Edge Ratio Parameter may be input by a user or administrator of an apparatus 1000, as described hereinabove. Preferably, an edge Ratio Parameter for an X-Ray image digital image may be set to 7.44.

In the Binary image, each pixel which is at least as intensive as the threshold is converted into a binary 1, and each pixel which is weaker than the threshold is converted into a binary 0.

Figure 5:
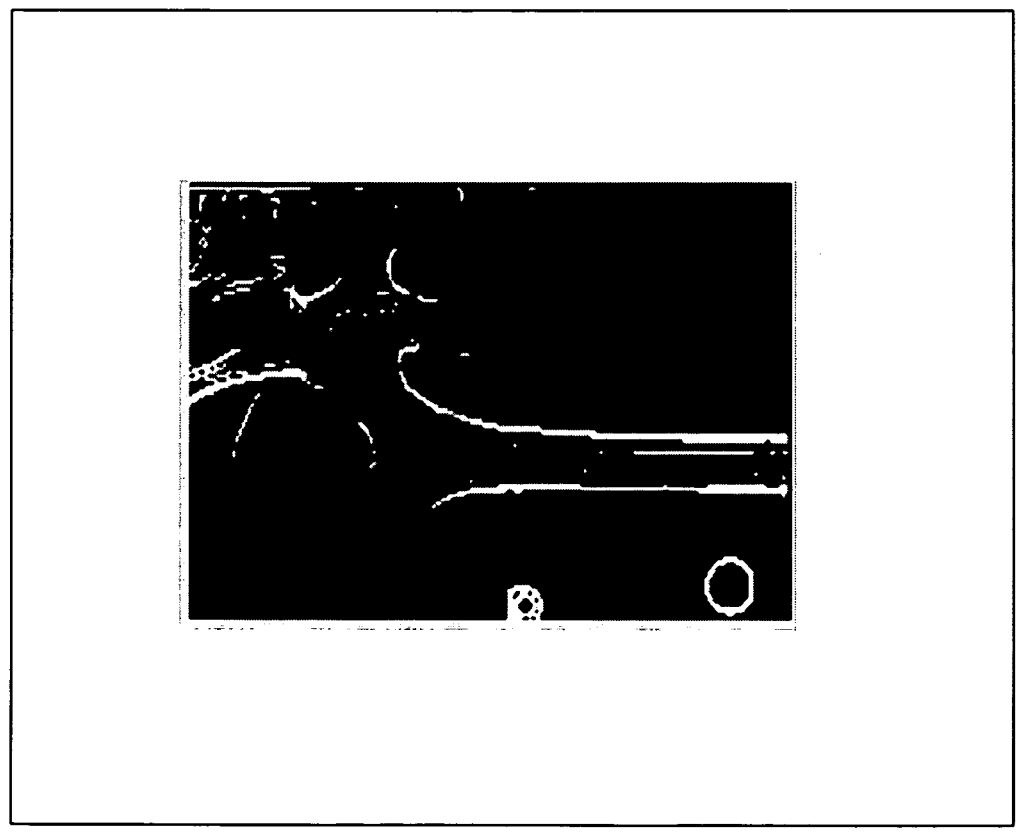

An exemplary binary image, according to a preferred embodiment of the present invention is shown in FIG. 5.

Next, the binary image is convolved using modified Hough Transformation 240 of the binary image, say using an image convolver, as described hereinabove. In the modified Hough Transformation 240, the binary image is convolved using a ring matrix.

Figure 6:
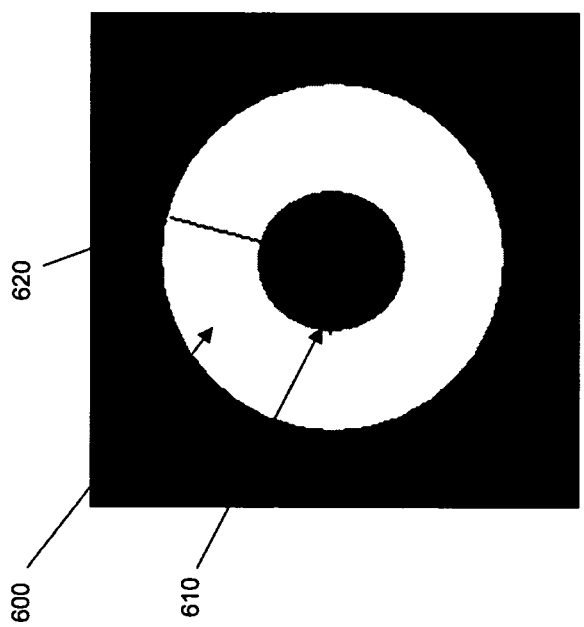

As illustrated in FIG. 6, the ring matrix consists of a ring area 600 confined by a first circle 610 which has a minimal radius predefined for the image of the spherical calibration marker. The ring area is also confined by a second circle 620, which is concentric to the first circle 610 and has a maximal radius predefined for the image of the spherical calibration marker.

In the ring matrix, each and every point between the two circles is a binary 1, while each remaining point is a binary 0.

The ring matrix may be mathematically defined using the formula:

$$C_{x,y} = r\_min^2 \leq (x - r\_max)^2 + (y - r\_max)^2 \leq r\_max^2 \begin{cases} 1 \\ 0 \end{cases}$$

$C_{x,y}$—denotes a point inside the ring matrix.

r_min—denotes the minimal radius predefined for the image of the spherical calibration marker. The minimal radius may be predefined by a user, say using the control unit 130 described hereinabove.

r_max—denotes the maximal radius predefined for the image of the spherical calibration marker. The maximal radius may be predefined by a user, say using the control unit 130 described hereinabove.

Figure 7:

An exemplary resultant convolved image is shown in FIG. 7.

After the Hough Transform is carried out, the image pixels may be ordered by intensity, and each pixel may be geometrically checked as a circle center. However, there is no need to have a full resolution of the convolved image, since the geometrical check may use any point inside the circle, and not necessarily the point in the very center of the circle.

Therefore, a resolution where each pixel is half the minimum radius is sufficient for the geometrical check.

By resizing the convolved image into an image having a resolution lower than the resolution of the convolved image, there may be needed fewer computations, as there is less data to be processed during the geometrical check. There may also be less circle centers to check. Furthermore, the likelihood of checking more than one point inside the same circle may be reduced.

The convolved image is resized 250, say by the image resizer described hereinabove. Preferably, the resizing is carried out using the Max Value Method.

The Max Value Method preserves the pixels that have the strongest intensity.

Each of the preserved pixels is regarded as a possible circle center. The Max Value Method produces an image having a lower resolution than the convolved image while at the same time retaining those of the highest intensity. Preferably, the Max Value method is carried out using a Zoom Factor calculated using the formula:

$$ZF = \frac{2 - \text{maximum circle radius}}{\text{minimum comprehendible radius} - \text{minimum circle radius}}$$

to produce a result which is (2/minimum circle radius) in comparison to the original image.

Figure 8:
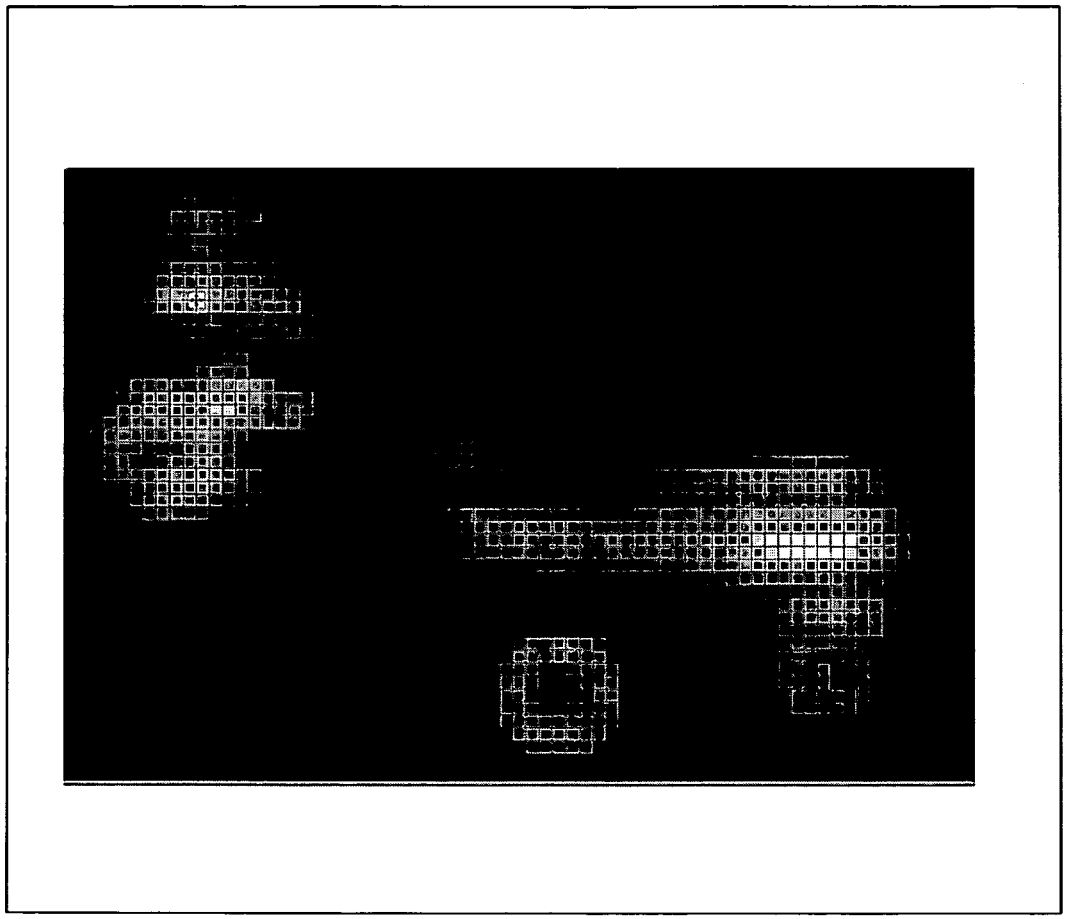

An exemplary resized convolved image, according to a preferred embodiment of the present invention, is provided in FIG. 8.

The pixels of the resized image are sorted 260 according to intensity of each pixel. Preferably, the sorted pixels are stored in an array list, as known in the art.

Next, there are selected a number (N) of strongest pixels amongst the sorted pixels as potential marker pixels. Optionally, the number (N) is a parameter value provided by a user of apparatus 1000, say using the control unit 130, as described in further detail hereinabove. Each of the N selected pixels is located in the received digital image.

Next, there is carried out a geometrical check in the received digital image. In the geographical check, each of the N selected pixels is examined 270 with respect to being positioned inside a circle, as described in further detail hereinbelow.

Finally, the found image of the spherical calibration marker in the received digital image is provided (or an indication that no such image is found in the digital received digital image).

Figure 9:
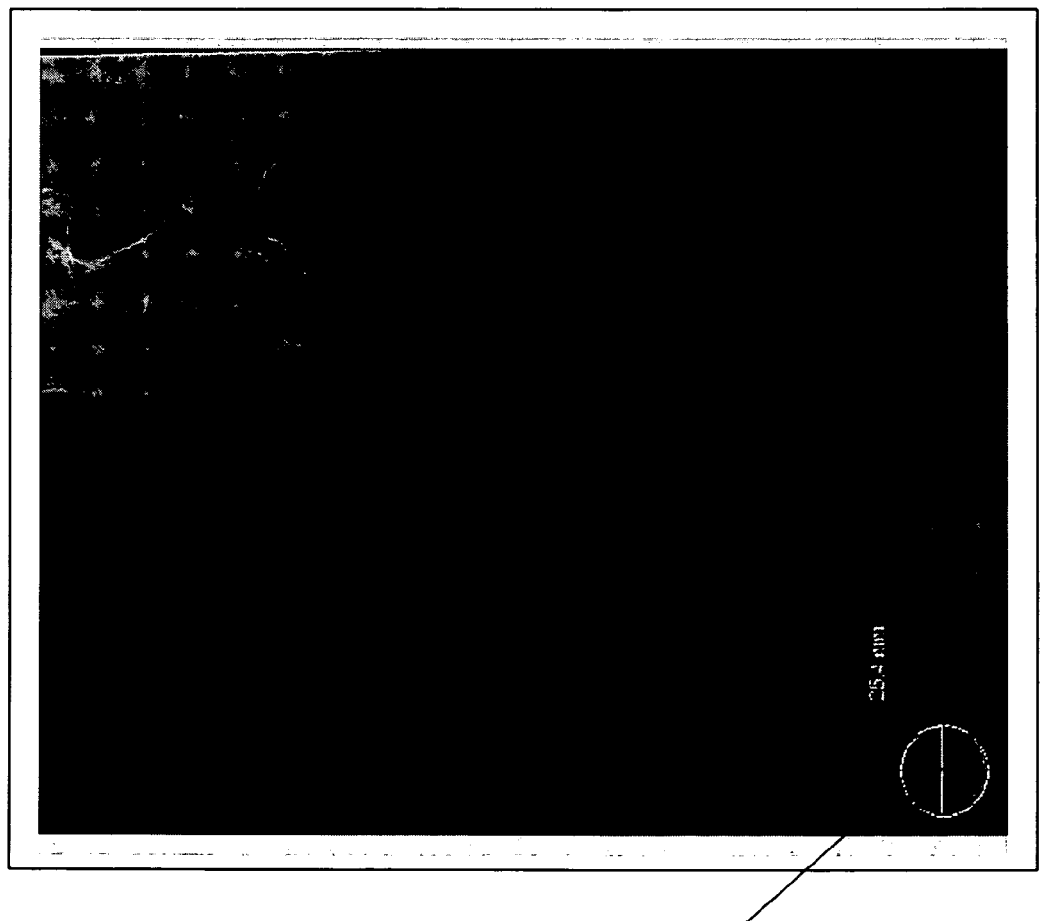

Reference is now made to FIG. 9, which shows an exemplary digital image with a spherical calibration object found on the image, according to a preferred embodiment of the present invention.

The spherical calibration marker 910 may be located on the selected pixels found to be positioned in a sphere. Preferably, the found calibration marker 910 is marked with data such as the marker's diameter etc, on the image, as illustrated in FIG. 9. The marking of the calibration marker may be carried out by the calibrator 160 described in further detail hereinabove.

Methods for Checking if a Pixel is Inside a Circle

Reference is now made to FIG. 10, which is an exemplary flowchart of a method for checking if a pixel is inside a circle, according to a preferred embodiment of the present invention.

According to a preferred embodiment, the user may be allowed to manually choose a point as a potential point inside a circle. Consequently, it is the user chosen point, rather than the N pixels selected as per the description above, that is checked with regards to positioning inside a circle, as described hereinbelow.

According to the method illustrated in FIG. 10, for each of the N pixels selected as per the description above, where N denotes the number of pixels to check for positioning inside a circle, there are carried out the following steps, say using the circularity finder, describe hereinabove:

First, each of the N selected pixels is positioned 1010 in the received digital image. That is to say, for each pixel there is found the co-ordinate location of the point represented by the pixel in the received digital image.

Next, there is cut a rectangle 1020 around the pixel from the received digital image. Preferably, the cut rectangle is the smallest possible rectangle which may contain a circular image of the spherical calibration marker. Preferably, the cut rectangle includes n pixels in each direction from the position of the pixel in the received digital image, where n=r_max−2*r_min Next, the cut rectangle is edge detected 1030, using the Canny Method or the Sobel Method.

In both methods, the rectangle is multiplied by a convolution matrix. Preferably, the convolution matrix is a 3×3 matrix. An exemplary 3×3 Sobel matrix for horizontal convolution (Gx), and an exemplary 3×3 Sobel matrix for vertical convolution (Gy) are shown in FIG. 11.

The product matrix resultant upon multiplying the rectangle cut from the received digital image and the horizontal matrix (Gx) and the product matrix resultant from multiplying the rectangle and the vertical matrix (Gy) are used to generate an edge direction map for the rectangle. For generating the edge map, the values in the product matrixes are processed using the formula, as known in the art:

$$\theta = \arctan(G_y/G_x)$$

θ denotes the angle representative of the edge direction in of a pixel in the cut rectangle.

$G_x$, $G_y$ denote value of a certain cell in the horizontal and vertical matrixes respectively.

In order to avoid generating an error whenever Gx is equal to zero, whenever the gradient in the x direction is equal to zero, the edge direction has to be equal to 90 degrees or 0 degrees, depending on the value of the gradient in the y-direction.

If Gy has a value of zero, the edge direction equals 0 degrees. Otherwise the edge direction equals 90 degrees.

Preferably, the edge direction is rounded into one of four possible directions when describing the surrounding pixels −0 degrees (in the horizontal direction), 45 degrees (along the positive diagonal), 90 degrees (in the vertical direction), or 135 degrees (along the negative diagonal), as illustrated in FIG. 12.

For example, if the orientation angle is found to be 3 degrees, the angle is rounded to zero degrees.

Next, edges surrounding each pixel in the rectangle are checked 1040 for forming a valid circle. Preferably, the edges are checked for forming a valid circle using the methods for checking circularity around a pixel described hereinbelow.

If the edges form a valid circle around the pixel 1050, the coordinates of the circle in the rectangle 1060 are offset, so as to compensate for displacement of the coordinates caused by the edge detection. The coordinates are further offset 1060 according to coordinates of the rectangle in the received digital image.

The coordinates of the rectangle are used to locate and mark 1070 the circle inside the image, as illustrated in FIG. 9 and described hereinabove.

Methods for Checking Circularity Around a Pixel

Reference is now made to FIG. 13 which is a flowchart illustrating a method for checking if edges surrounding a pixel form a circle, according to a preferred embodiment of the present invention.

For every angle around the pixel, in steps of (2π/a predefined number of points to check 1310), there are performed the following steps:

First, there is carried out a geometrical check 1320.

In the geometrical check 1320, a line is drawn from the position of the pixel, in the direction defined by the angle calculated by (2π/the number of point checked).

The strongest intensity points (or pixels) on the drawn line are selected for further processing. Preferably, only points having a gradient in a direction expected for a circle formed around the pixel are selected for further processing, as shown in FIG. 14.

An exemplary mathematical algorithm for geometrically checking circularity around a pixel, according to a preferred embodiment of the present invention, is illustrated in FIG. 15.

Next, there is carried out statistical confirmation 1330 based on the points selected using the geometrical method described hereinabove. Selected ones of the points are than determined 1340 to form a circle surrounding the pixel.

Reference is now made to FIG. 16, which is a flowchart illustrating a method for statistically confirming circularity, according to a preferred embodiment of the present invention.

First, there are listed (4.4) all three point combinations amongst the selected points.

Preferably, combinations which are mere re-arrangements of each other are listed only once, say using the combinatory formula:

$$VerifyWith = \frac{(Points2Check \cdot VerifyPart)!}{(Points2Check \cdot VerifyPart - 3)!}$$

Ponts2Check denotes the number of rays to extend from the proposed circle center in the geometric check of the image.

VerifyPart denotes the part of the rays drawn that is needed to verify the circle center. (For example, 0.7 indicates that 70% of points are needed to verify the circle center)

Each listed combination of three points is determined to define a circle, if the circle radius is not smaller than r_min (defined hereinabove), and not larger than r_max (defined hereinabove). In order to define a circle, the center of the circle defined by the three points has to be at the position of the pixel supposed to be inside the circle r_max (defined hereinabove) (4.4.1).

Preferably the combinations forming a circle are stored in a Hash Table. The Hash Table may be implemented using a class with a Hash provider that creates a different Hash key for every combination of a center point and a radius, with a sensitivity of one pixel. One way to achieve such sensitivity is to divide the center coordinates and radius by two, and floor the float result.

An exemplary Hash Class written in the C# Programming Language, according to a preferred embodiment of the present invention is provided in FIG. 17.

If a Hash key created for a circle created from a certain three point combination does not exist as a key in the Hash Table, the key is inserted (4.4.2) into in the Hash Table, and a counter for the key is set in the Hash Table to One.

If the Hash key created for the circle already exists, the counter for the key in the Hash Table is increased by one (4.4.3).

For example, in FIG. 14, one can see that all the combinations of points that do not include points 2 and 3 add up to the same circle parameters in a histogram which may be generated using a Hash Class, as described hereinabove.

The combination corresponding to the key having the highest counter (4.4.4) in the Hash Table represents a potential circle usable for locating the image of the spherical calibration marker.

If the counter is higher than a predefined minimal number of points, it is determined that the key associated with the counter represents a possible image of the spherical calibration image (4.5). The points forming the circle may be used for locating the spherical calibration marker.

It is expected that during the life of this patent many relevant devices and systems will be developed and the scope of the terms herein, particularly of the terms "Radiographic Image", "Digital Image", "Calibration Marker", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. Apparatus for calibration of radiographic images, the images comprising a spherical calibration marker appearing therein, the apparatus implemented on an electronic processor and comprising:
   a) an image receiver, configured to receive a radiographic image with said spherical calibration marker appearing therein; and
   b) a marker finder, associated with said image receiver and configured to automatically find an image of the spherical calibration marker in the received image by:
   edge detecting the image,
   forming a binary image from the edge detection, the binary image being formed by defining pixels therein either as a first value indicating belonging to an edge or to a second value indicating not belonging to an edge; pixels in said binary image corresponding to pixels detected as edges being set to said first value, and
   testing respective pixels of said binary image to determine whether a circle of said pixels of said first value belonging to an edge is described around a respective pixel in said binary image, and if so, setting said edge as a detected circle for calibration, wherein said testing comprises:
   stepwise around said pixels belonging to said edge selecting pairs of pixels and a presumed center pixel and following said selecting, pairwise testing said pairs of pixels for having a radius about said presumed center pixel, setting a key and a counter for each combination of center and radius and applying a respective counter for pixel pairs that share a same radius and center, and then, using said keys and counters, selecting as the detected circle that circle on which lies the largest number of said pairs of pixels which share a same center and radius; and
   c) a calibrator associated with the marker finder, for using said detected described circle and respective pixel as a centered circle and calibrating said image.

2. The apparatus of claim 1, further comprising a digitizer, associated with said image receiver and configured to digitize the image, thereby to provide a digitized image for processing by said marker finder.

3. The apparatus of claim 1, further comprising an image downsizer, located prior to said marker finder, configured to downsize the image into a downsized image having a smaller number of pixels than the image.

4. The apparatus of claim 3, wherein the image downsizer is further configured to downsize the image using a zoom factor based on a predefined maximal expected radius and a minimal comprehensible radius, said radiuses pertaining to said image of the spherical marker.

5. The apparatus of claim 4, wherein said minimal comprehensible radius is a radius of a smallest circle presentable on a monitor screen.

6. The apparatus of claim 3, wherein said marker finder is associated with an edge detector, configured to detect edges in said downsized image.

7. The apparatus of claim 6, wherein said marker finder is associated with an image converter, configured to convert said edge detected image into said binary image, by applying a predefined threshold on intensity of each pixel of said edge detected image.

8. The apparatus of claim 6, wherein said marker finder is associated with an image converter, configured to convert said edge detected image into said binary image, by applying a threshold on intensity of each pixel of said edge detected image, wherein said threshold is a quotient of intensity of most intensive pixel of said edge detected image and a predefined edge ratio.

9. The apparatus of claim 8, wherein said edge ratio is 7.44.

10. The apparatus of claim 7, further comprising an image convolver, configured to convolve said binary image using a ring matrix, said ring matrix consisting of a ring area confined by a first circle having a minimal radius predefined for said image of said spherical calibration marker, and by a second circle being concentric to said first circle and having a maximal radius predefined for said image of said spherical calibration marker.

11. The apparatus of claim 10, further comprising an image re-sizer, configured to resize said convolved binary image to preserve pixels having respectively strong intensities, thereby to generate a resized image having a lower resolution than said convolved image but retaining highest edge intensities.

12. The apparatus of claim 1, wherein said marker finder is associated with a pixel selector, the pixel selector being configured to sort pixels of said image according to intensity of each of said pixels of said image, and to select a predefined number of strongest ones of said sorted pixels as potential marker pixels.

13. The apparatus of claim 12, wherein said marker finder is further associated with a circularity finder, configured to locate each of said selected pixels in the image, and to identify which of said potential marker pixels is positioned in said circle.

14. The apparatus of claim 13, wherein said marker finder is further configured to locate said spherical calibration marker on said selected pixels found to be positioned in a circle.

15. The apparatus of claim 1, further comprising a control unit, operable for controlling the apparatus.

16. The apparatus of claim 1, further comprising a user interface manager, configured to manage an interface between the apparatus and a user.

17. Method for calibrating radiographic images, the images comprising a spherical calibration marker appearing therein, the method comprising:
   a) receiving the image; and
   b) automatically finding an image of the spherical calibration marker in the received image, said finding comprising
      edge detecting the image,
      forming a binary image from the edge detection, by setting each pixel corresponding to a detected edge to a first value indicating an edge, all other pixels being set to a second value indicating non-edge,
      testing respective pixels of said binary image to determine a circle that is described by set pixels set as edge pixels, around said respective pixel in said binary image, wherein said testing comprises:
         stepwise around said edge pixels selecting pairs of said edge pixels and a presumed center pixel;
         subsequent to said selecting, pairwise testing said selected pixel pairs for sharing a radius about said presumed center pixel;
         from the tested pairs, setting keys and using counters respectively for each instance of a shared center and radius, and selecting a largest number of said pairs which share a same center and radius; and
         setting the center and radius shared by said largest number of pixels as said described circle, and
   c) calibrating said image based on said described circle.

18. The method of claim 17, further comprising a step preceding finding said marker of digitizing the image.

19. The method of claim 17, wherein said finding includes a preceding step of downsizing the image into a downsized image having a smaller number of pixels than the image.

20. The method of claim 19, wherein said detecting edges is carried out in said downsized image.

21. The method of claim 20, wherein said finding further includes a step of converting said edge detected image into said binary image, by applying a predefined threshold on intensity of each pixel of said edge detected image.

22. The method of claim 21, wherein said finding further includes a step of convolving said binary image using a ring matrix, said ring matrix consisting of a ring area confined by a first circle having a minimal radius predefined for said image of said spherical calibration marker, and by a second circle being concentric to said first circle and having a maximal radius predefined for said image of said spherical calibration marker.

23. The method of claim 22, wherein said finding further includes a step of resizing said convolved binary image preserving pixels of said convolved binary image having a highest intensity.

24. The method of claim 23, wherein said finding further includes sorting pixels in said resized image according to intensity of each of said pixels of said resized image, and selecting a predefined number of strongest ones of said sorted pixels as potential marker pixels.

25. The method of claim 24, wherein said finding further includes locating each of said selected pixels in the image and finding if each of said potential marker pixels is positioned in said circle.

26. The method of claim 25, wherein said finding further comprising locating said spherical calibration marker on said selected pixels found to be positioned in a circle.

27. Method for calibrating an image, the image comprising a spherical marker, the method comprising:
   a) taking a picture of a person with the spherical marker positioned in proximity of said person, thereby generating the image;
   b) automatically finding an imprint of the spherical marker in the image; and
   c) calibrating the image utilizing said found image of the spherical marker, wherein said automatically finding comprises:
      edge detecting the image,
      forming a binary image from the edge detection by setting each pixel corresponding to a detected edge to a first value indicating an edge, all other pixels being set to a second value indicating non-edge,
      pairwise testing pixels of said detected edge to determine whether a circle is described by respective pixels of a given pair set to the value of edge, around a presumed center pixel in said binary image, wherein said testing comprises:
      stepwise around said edge pixels selecting pairs of said detected edge pixels and said presumed center pixel; and
      subsequent to said selecting, carrying out said pairwise testing of said pairs of edge pixels and said presumed center for sharing a radius;
      setting a key for each presumed center and radius;
      using counters per key to count each pair sharing a radius and a center;
      from said counters, finding a single circle shared by a largest number of said pairs of edge pixels and said presumed center;
      selecting said single circle as said described circle, with said presumed center pixel as a circle center, and calibrating said image using said described circle.

* * * * *